United States Patent [19]

Belardinelli et al.

[11] Patent Number: 4,980,379

[45] Date of Patent: * Dec. 25, 1990

[54] USE OF ADENOSINE ANTAGONISTS IN THE TREATMENT OF BRADYARRHYTHMIAS AND HEMODYNAMIC DEPRESSION ASSOCIATED WITH CARDIOPULMONARY RESUCITATION AND/OR CARDIOVASCULAR COLLAPSE

[75] Inventors: Luiz Belardinelli, Gainesville, Fla.; Robert C. Wesley, Jr., Charlottesville, Va.

[73] Assignee: The University of Virginia, Charlottesville, Va.

[*] Notice: The portion of the term of this patent subsequent to Feb. 27, 2007 has been disclaimed.

[21] Appl. No.: 213,937

[22] Filed: Jun. 30, 1988

[51] Int. Cl.$^5$ .............................................. A61K 47/00
[52] U.S. Cl. .................................................. 514/821
[58] Field of Search ......................... 424/263; 514/821

[56] References Cited

PUBLICATIONS

Rahimtoola, S. H., J. Am. Med. Assoc., 247 pp. 2485–2890 (1982).
Iseri, L. T., Am. Int. Med. 88 pp. 741–745, 1978.

Primary Examiner—Paul J. Killos
Attorney, Agent, or Firm—Oblon, Spivak, McClelland, Maier & Neustadt

[57] ABSTRACT

A method to enhance the efficacy of cardioversion, defibrillation, cardiac pacing, and cardiopulmonary resuscitation and to treat post-resuscitation asystole, bradyarrhythmias, electromechanical dissociation, and hemodynamic collapse by administering to a human or animal an effective amount of an adenosine antagonist that competitively inhibits adenosine or that reduces the level of adenosine present in myocardial and vascular tissues and associated fluids.

35 Claims, 7 Drawing Sheets

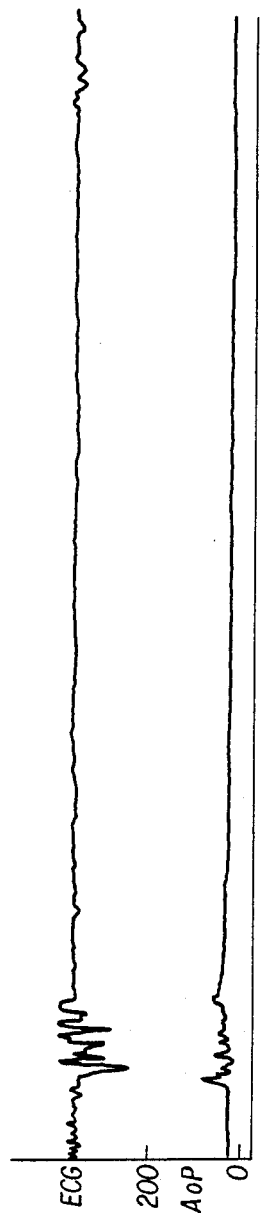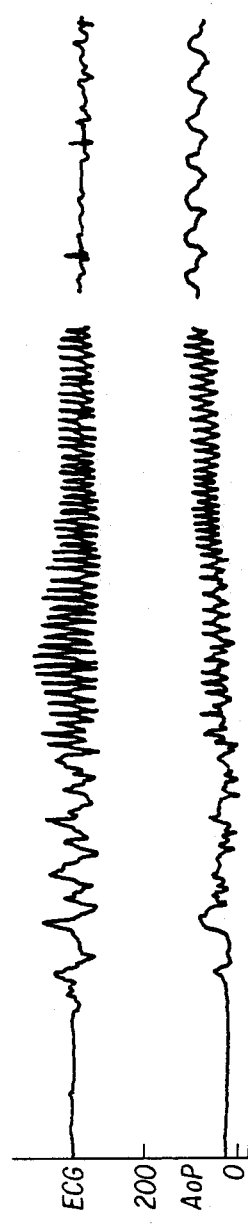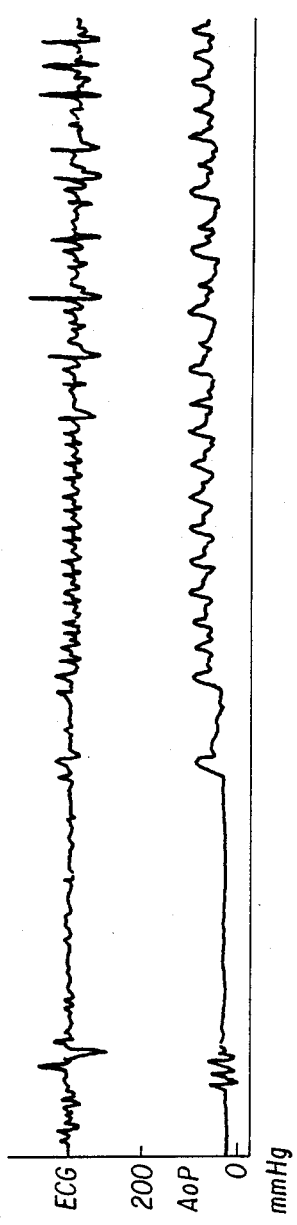
FIG. 6A POST DPM
FIG. 6B 4-DPPC INJ.
FIG. 6C POST 4-DPPC

POST DPM

4-DPPC INJ.

POST 4-DPPC

USE OF ADENOSINE ANTAGONISTS IN THE TREATMENT OF BRADYARRHYTHMIAS AND HEMODYNAMIC DEPRESSION ASSOCIATED WITH CARDIOPULMONARY RESUCITATION AND/OR CARDIOVASCULAR COLLAPSE

BACKGROUND OF THE INVENTION

1. Field of the Invention

The invention relates to the use of adenosine antagonists, either alone or in combination with pharmacologic possessing α and/or β-adrenergic or dopaminergic properties, to treat cardiac rhythm disturbances, mechanical dysfunction and hypotension and to facilitate cardioversion and/or defibrillation in the setting of cardiopulmonary resuscitation and/or cardiovascular cellapse.

2. Discussion of the Background

Prolonged cardiopulmonary resuscitation for ventricular fibrillation is associated with the occurrence of asystole or severe bradycardias and profound hemodynamic collapse associated with a severe depression in myocardial contractility (electromechanical dissociation) which are usually resistant to therapy. (Rahimtoola S. H., *J. Am. Med. Assoc.*, 247, pages 2485–2890 (1982) and Iseri, L. T., *Ann. Int. Med.*, 8, pages 741–745 (1978).)

Catecholamines and/or para-sympatholytic agents have traditionally been used to treat intractable ventricular fibrillation and post-defibrillation depressions in automaticity, cardiac conduction, and overall hemodynamic collapse. However, these agents are often ineffective, particularly in the setting of prolonged ventricular fibrillation and, as a consequence of their use, may provoke intractable ventricular fibrillation followed by death or severe neurological impairment. See McIntyre, K. M., Lewis, A. J., Eds, *Textbook of Advanced Life Support,* Vol 9, American Heart Association (1981) and *Am. Heart J.*, 97, 225–228 (1979).

Pharmacological agents are routinely used in the cardiopulmonary resuscitation of patients suffering from cardiac arrest. A review of these pharmacologic agents can be found in Otto C. W., *Circ.* 74 (*supplement IV*), IV-80–85 (December 1986). It has been established that the most significant factor in the return of spontaneous circulation during cardiopulmonary resuscitation is the enhancement of α-adrenergic tone, i.e., an increase in aortic diastolic pressure and coronary perfusion pressure. However, there has been no suggestion that the use of α-adrenergic agents improve survival relative to the use of epinephrine, a mixed adrenergic agonist with known deleterious effects.

Additionally, there is no clear evidence that epinephrine, the currently recommended pharmacologic agent, can increase the effectiveness of electric shock during the fibrillation.

Lidocaine is the recommended anti-arrhythmic agent for use during cardiac arrest. It is known however that lidocaine can increase the threshhold for defibrillation. Under experimental conditions, the anti-arrhythmic drug, Bretylium, seems to facilitate defibrillation; however, clinical data are less convincing. (Jaffe A. S., *Circ.* 74 (*supplement IV*), IV-70–74, December 1986).

The model established by the present inventors confirms that the cardioversion of prolonged hypoxic ventricular fibrillation is accompanied by cardiovascular collapse and depressions in cardiac automaticity, conduction, and contractility. This post-shock hypoxic depression is due, in part, to the collapse in arteriolar tone possibly mediated by the release of endogenous adenosine. In addition, the release of endogenous adenosine from myocardium might selectively dilate coronary resistance vessels promoting hypoperfusion of the subendocardial layer of the heart, the most distal and thus vulnerable cardiac vascular bed. The result would be enhanced ischemicinduced depression in contractility. Endogenous catecholamines are known to be released with vascular collapse and perhaps in response to an electrical shock. The beneficial vasomotor and inotropic effects of endogenous catecholamine release may, in turn, be attenuated by the anti-adrenergic action of endogenous adenosine. The aforementioned potential deleterious effects of endogenous adenosine may be reversed by adenosine antagonism. Thus, adenosine antagonism represents an important new therapy in the amelioration of the overall hemodynamic state during cardiopulmonary resuscitation and following defibrillation and, thus, would be expected to enhance survival of cardiac arrest victims. This concept has never been proposed.

It is known that endogenous adenosine can depress the electrical conduction through the atrioventricular (A-V) node, and that adenosine antagonism can reverse this phenomenom. U.S. Pat. No. 4,364,922 discloses a method of treating atrioventricular conduction block using adenosine antagonists. However, A-V conduction disturbances play only a small role in the overall constellation of factors which characterize brady-asystolic arrest. The more predominant factors noted in the clinical sector include profound bradycardia associated with junctional and ventricular escape rhythms, and hemodynamic depression secondary to vascular collapse and severe inotropic dysfunction (see Iseri, L.T. et al, loc cit). The use of adenosine antagonism to reverse these phenomena in the setting of prolonged cardiopulmonary resuscitation has never been proposed.

Accordingly, there exists a need for a more effective pharmacologic method of treating the bradyarrhythmias associated with prolonged cardiopulmonary resuscitation. In addition, there exists a further need for a method of treating these arrhythmias which does not evolve into intractable ventricular fibrillation.

In addition to the aforementioned, the inventors have found that adenosine antagonism lowers the threshold current required for defibrillation following prolonged canine ventricular fibrillation and thereby increases the effectiveness of electric shock therapy. Thus, an intravenously administered form of adenosine antagonism may be important in reducing the duration of ventricular fibrillation, a prognostic factor known to enhance survival in the setting of cardiac arrest and resuscitation. In addition, an orally administered and longer-acting form of adenosine antagonism may be important in lowering the energy and current requirements of shock therapy administered by implanted electrodes, increase the efficacy of electric shock, and reduce the energy expenditure of automatic implantable defibrillators and, thus extending the device's battery life and battery replacement schedule. Adenosine antagonism may also lower the threshold current for cardiac pacing via endocardial and epicardial electrode placement or via transthoracic pacing electrodes. In addition to intravenous and oral forms, a local sustained release form of adenosine antagonist may be incorporated into the electrode tips of endocardial and epicardial leads for the purpose of lowering pacing thresholds.

At present there are no claims in the medical literature divulging the use of adenosine antagonism to lower energy and current requirements for cardio-version, defibrillation, and cardiac pacing. Kralios et al (Am Heart J: 105(4): 580–586) infused exogenous adenosine into canine coronary arteries and demonstrated a reduction in the threshold current necessary to induce ventricular fibrillation. However, the authors conclude "physiologic or pharmacologic coronary vasodilation without evidence of concomitant myocardial hypoxia" may contribute to the electrical instability resulting in ventricular fibrillation. No claim was made that the release of endogenous adenosine during the conditions of anoxia or hypoxia mediated such electrical instability or that antagonism of endogenously released adenosine would promote ventricular defibrillation. Ruffy et al (J. Am. Coll. Cardiology 9(2): 142A, 1987) showed that aminophylline (10 mg/Kg IV) lowered defibrillation threshold in conscious dogs. However, defibrillation energy is a poor descriptor of the electrical requirement for defibrillation compared to current (Lerman et al. J. Clin. Invest. 80: 797–803, 1987). Aminophylline is a relatively weak adenosine antagonist with well established effects on phosphodiesterase inhibition. The authors did not correlate effects on defibrillation threshold with serum levels of aminophylline. At a dose of 10 mg/Kg, the authors could not and did not claim that the effect of aminophylline was mediated via adenosine antagonism.

Additionally, the inventors have demonstrated in a pentobarbital anesthetized dog that 8-phenylsulfonyltheophylline (8-PST) (5 mg/Kg IV) significantly reduced the number of current-based countershocks required to terminate ventricular fibrillation of 2 mins. duration. In contrast to aminophylline, 8-PST is highly specific for competitive adenosine antagonism and causes no significant inhibition of phosphodiesterase activity (Clemo, SHF and L Belardinelli, 1985). A comparative study of antagonism by alkylxanthines on the negative dromotropic effect of adenosine and hypoxia in isolated guinea-pig hearts is disclosed in Current Clinical Practice Series No. 19: Anti-asthma Xanthines and Adenosine, K. E. Anderson and C. Kong, Princeton, Sydney, Tokyo, pp. 417–422; and F. W. Smellie, C. W. Davis, J. W. Daly, and J. N. Wells, 1979. Alkylxanthine inhibition of adenosine-elicited accumulation of cyclic AMP in brain slices and of brain phosphodiesterase activity is disclosed in Life Sci. 24:2475–2482. Thus, we claim that the observed effect is mediated by adenosine antagonsim and is consistent with our other experimental observations. Since no convincing clinical data exist establishing the efficacy of presently available pharmacologic agents in reducing threshold currents for defibrillation, we propose that there exists a need for such an agent.

SUMMARY OF THE INVENTION

Accordingly, one object of the present invention is to provide a method of treating post-resuscitation bradyarrhythmias, hemodynamic collapse, and electromechanical dissociation associated with prolonged cardiopulmonary resuscitation.

Another object of the invention is to provide a method of treating bradyarrhythmias, hemodynamic depression, and contractile dysfunction associated with hypoxemia needs as might occurred during cardiovascular collapse e.g. of cardiogenic, septic, hypovolemic or hemorrhagic shock).

A further object of the invention is to promote the efficiency of cardiopulmonary resuscitation itself by altering the potential deleterious vasomotor effect of endogenously released adenosine. The invention thus promotes the maintenance of aortic diastolic pressure and coronary perfusion pressure and reverses harmful hypoperfusion of the subendocardium mediated by an adenosine-induced coronary "steal" phenomenon.

A further object of the invention is to provide a pharmacologic method for lowering the threshold current and energy for defibrillation thus enhancing the efficacy of defibrillation and/or cardioversion. One mechanism whereby this is accomplished is by favorably altering peripheral and cardiac vasomotor tone.

Another object of the invention is to provide a pharmacologic method for lowering the current and energy requirements for cardiac pacing (via transthoracic, epicardial, or endocardial electrodes) in the setting of resuscitation.

A further object of the invention is to provide a method of preventing and/or treating post-resuscitation asystole and bradyarrhythmias by using a pharmacologic agent which lowers the threshhold for defibrillation and thus, shorten the duration of ventricular fibrillation.

A further object of the invention is to provide a method preventing and/or (treating of post-resuscitation arrhythmias with adenosine antagonists.

These and other objects of the present invention which will become apparent from the following detailed description have been achieved by the present method, comprising this step of:

administering to a human or animal during or after cardiopulmonary resuscitation and/or cardiovascular collapse an amount of an adenosine antagonist sufficient to alleviate post-resuscitation bradyarrhythmias and hemodynamic collapse.

Note these aforementioned objects and methods are proposed for potential use either alone or in combination with $\alpha$- and/or $\beta$-adrenergic or dopaminergic agents with the possibility of lowering doses required and avoiding potential dose-dependent side-effects while maintaining or enhancing efficacy.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6 illustrates the reversal of porcine post-defibrillation electrophysiologic and hemodynamic depression by 4-DPPC in the presence of dipyridamole. Panels A and C display post-shock sequelae following 45 secs of ventricular fibrillation (VF) after the intravaneous infusion of dipyridamole (6.5 mg) during concomitant infusion of methoxamine 0.015 mg kg$^{-1}$ min$^{-1}$.

40A shocks were delivered at the arrows. Panel A: Effect of Dipyridamole. Complete atrioventricular (AV) block without an escape rhythm is displayed. The aortic pressure (AoP) at the end of 15 secs was 20 mmHg. Panel B: Reversal of depression following 4-DPPC injection. 4-DPPC (5 mg kg$^{-1}$) is injected prior to beginning of the panel (30 secs post-defibrillation). Chest compression is initiated for less than 30 secs. At the rightward panel, the sinus cycle length SCL and AoP were 400 msecs and 125/95 mmHg, respectively. Panel C: Prevention of depression after 4-DPPC pretreatment. Following defibrillation, transient 3:1 block gives way to sinus rhythm and an AoP of 125/90 mmHg at 15 secs post-defibrillation. Short episodes of ventricular begeminy and nonsustained ventricular tachycardia were noted at the end of the tracing.

DETAILED DESCRIPTION OF THE PREFERRED EMBODIMENTS

Figure 1A:
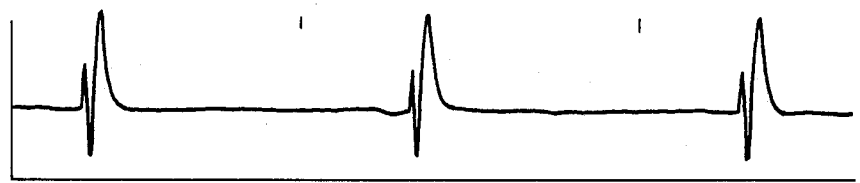
FIG. 1 illustrate of intravenous 8-PST (5 mg/Kg) infusion on canine post defibrillation heart rate and rhythm (Group A). Panel A: Sinus arrest and junctional rhythm (cycle length =2880 msecs) prior to 8-PST infusion. Panel B: Sinus rhythm (cycle length =1240 msecs) at 15 secs, after rapid 8-PST infusion.

The present invention has succeeded in providing a method for the treatment of post-resuscitation bradyarrhythmias and hemodynamic collapse associated with prolonged cardiopulmonary resuscitation from ventricular fibrillation and/or cardiac arrest. The inventors have discovered that endogenous adenosine not only depresses the atrioventricular (AV) nodal conduction but also is associated with the post-shock hypoxic depression of automaticity, contractility and hypotension of heart muscle. It has also been discovered that adenosine antagonism can reverse such depression and restore normal electrophysiologic and hemodynamic function in a short period of time. Thus, the invention involves the use of an adenosine antagonist, either alone or in combination with pharamacologic agents possessing α- and/or β-adrenergic or dopaminergic properties, to treat cardiac rhythm disturbances, mechanical dysfunction and hypotension and to facilitate cardioversion and/or defibrillation during and/or after cardiopulmonary resuscitation.

By "adenosine, antagonists" is meant any agent which acts by whatever mechanism to reduce the effect or the interstial concentration of adenosine in myocardial tissue. An antagonist of adenosine may be a competitive inhibitor or a substance that reduces the concentration of adenosine by destroying adenosine or that causes its destruction by altering metabolic pathways normally present in cells or extracellular fluid. An irreversal inhibitor is not suitable for the present invention since the action of adenosine performing its inherent regulatory functions must not be permenantly impaired. Examples of known adenosine antagonists are the xanthines, alkylxanthines, for example, propylxanthines and methylxanthines (e.g., 8-(p-sulfophenyl)theophylline) and the novel non-xanthine adenosine antagonists (e.g., imidazopyrimidine, pyrazolopyridine, etazolate, pyrazoloquinoline, and triazoloquinazoline (Pflugers Archiv 407: S31, 1986).

Preferred examples of methylxanthines are 1,3,7-trimethylxanthine (caffeine); 3,7-dimethylxanthine (theobromine); 1,3-dimethylxanthine (theophylline); aminophylline; and the xanthine derivatives disclosed in the specification of U.S. Pat. No. 4,364,922 incorporated herein by reference. Preferred propylxanthines are (E)-4-(1,2,3,6-tetrahydro-1,3-dimethyl-2,6-dioxo-9H-purin-8-yl)cinnamic acid and (E)-4-(1,2,3,6-tetrahydro-2,6-dioxo-1,3,dipropyl-9H-purin-8-yl)cinnamic acid. The method of synthesizing the xanthine is not critical and can be performed by any known method of synthesizing these compounds, for example, the method disclosed in U.S. Pat. No. 4,364,922.

(E)-4-(1,2,3,6-tetrahydro-1,3-dimethyl-2,6-dioxo-9H-purin-8-yl)cinnamic acid and the corresponding dipropyl derivative whose structures are shown below may be synthesized from the corresponding uracil and formylcinnamic acid compounds.

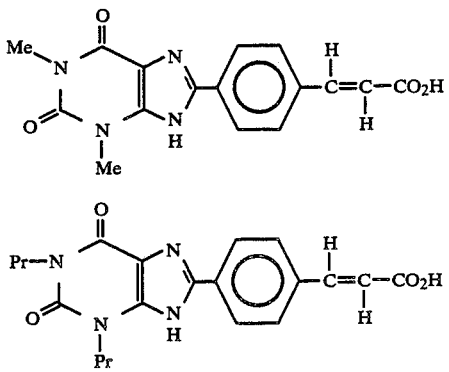

The method of the present invention relates to the enhancement of the efficacy of cardiopulmonary resuscitation and to the treatment of post-resuscitation asystole, bradyarrhythmias, electro-mechanical dissociation, and hemodynamic collapse. The method also relates to the lowering of energy and current requirements for defibrillation, cardioversion, and cardiac pacing in the setting of resuscitation.

The adenosine antagonists used in the present method may be used alone or in combination with agents possessing α- and/or β-adrenergic or dopaminergic properties. Preferred examples of α-adrenergic agents are epinephrine, norepinephrine, phenylephrine, metaraminol, and methoxamine. Preferred examples of β-adrenergic agents are epinephrine, norepinephrine, and isoproterenol. Preferred examples of dopaminergic agents are dopamine and dobutamine.

Dosages of the adenosine antagonists for treating post-resuscitation cardiac arrhythmias fall within the range of 0.1–20 mg/kg. An effective dose may be recognized by the alleviation of bradycardia and reversal of hemodynamic collapse.

Standard procedures for administration of adenosine antagonists such as theophylline and aminophylline at effective dosage levels are well established and are well known to those skilled in the art. For example, the recommended therapeutic range for plasma levels of theophylline for patients with reversible obstruction of the airways is from 10–20 μg/ml.

Similar plasma levels are suggested above for the treatment of the resuscitation and post-resuscitation state. These plasma levels may be established by standard methods of administration, including but not limited to intravenous injection, oral injestion via tablets, capsules, or liquids, suppository implantation, intramuscular injection, inhalation and the local release from implanted electrodes. Any of these methods, which are able to provide the proper plasma level are suitable for the present invention. The locally released preparations would not require systemic concentrations or effects to obtain the desired ac ion of optimizing electrode efficacy. The preferred method of adminstration is intravenous injection for resuscitation and post-resuscitation states. Intravenous administration of the adenosine antagonists and/or α-adrenergic or β-adrenergic or dopaminergic agents may consist of a single injection, a loading dose followed by continuous administration of the lower level maintenance dose, injection spaced over a period of time, continuous injection of a low level maintenance dose, injection spaced over a period of time, continuous injection of a low level maintenance dose, or other types of administration that are suitable for the particular needs of the individual human or animal being treated. Dosages of theophylline and aminophylline required for specific plasma levels are well known to those in the art, as shown in the article "Rational Intravenous Dosages of Aminophylline" by Mitenko and Ogilvie, New England J. Med., 289, pages 600–603 (1973). For example, to achieve a theophylline plasma level of 10 μg/ml, theophylline is administered in an initial loading dose of 5–6 mg/kg followed by a continuous maintenance dose of 0.90 mg/kg/hr.

Administration of these amounts is-sufficient for achieving and maintaining a plasma level of 10 μg/ml for any method in which theophylline or a derivative is absorbed into the blood stream without being destroyed. Nonlimiting examples include intravenous injection, absorption by the large intestine from suppositories, absorption by the small intestine from capsules that release theophylline or other adenosine antagonists in the intestine after passing through the stomach, or absorption through the lungs. Methods that require the adenosine antagonists to pass through the stomach may be subject to destruction of the antagonists and accordingly must be either protected in a form that is not destroyed in the stomach or administered in a large dose so that the amount reaching the blood stream is sufficient to achieve the desired effective level.

When the adenosine antagonists is administered with an α-adrenergic or β-adrenergic or dopaminergic agent, the relative ratio of these two components should be in the range of 0.01:1.0 to about 1.0:0.01.

The pharmaceutical compositions of the present invention may contain one or more adenosine antagonists as well as one or more α-adrenergic and/or β-adrenergic or dopaminergic agents. The pharmaceutical preparations may be prepared in any of the customary methods well known in the art.

The adenosine antagonists may be admixed with any pharmaceutically acceptable carrier or carriers, such as water, ethanol, inert solids or any other carrier customarily used for the type of administration in question.

The method of the present invention may be used in the treatment of humans and in the practice of veterinary medicine on warm blooded mammals. Examples of mammals which may be treated include cats, dogs, horses, etc.

Other features of the invention will become apparent in the course of the following descriptions of exemplary embodiments which are given for illustration of the invention and are not intended to be limiting thereof.

EXAMPLES

EXAMPLE 1

Preparation of (E)-4-(1,2,3,6-tetrahydro-1,3-dimethyl-2,6-dioxo-9H-purin-8-yl) cinnamic acid (4-DMPC)

5,6-Diamino-1,3-dimethyluracil hydrate (1.70 g, 10.0 mmol) and 4-formylcinnamic acid (1.76 g, 10.0 mmol) were refluxed in acetic acid (10 mL)-methanol (100 mL) for 0.5 hour. (E)-4[(6-Amino-1,2,3-4-tetrahydro-1,3-dimethyl-2,4-dioxo-5-pyrimidinyl)iminomethyl]cinnamic acid was precipitated as a yellow powder (1.84 g, 56%); mp 299°–301° C. with effervescence. Analysis for ($C_{16}H_{16}N_4O_4$): C,58.53;H,491;N,1707. Found: C,58.36;H,4.93;N,16.90. The structure was confirmed by H-NMR and EI mass spectrum. The (E)-4-[(6-amino-1,2,3,4-tetrahydro-1,3-dimethyl-2,4-dioxo-5- pyrimidinylmethyl]cinnamic acid (500 mg, 1.52 mmol) was then refluxed in nitrobenzene (125 mL) for 2.5 hours with slow distillation to remove water formed. The reaction mixture was cooled and the precipitate washed with ether. Recrystallization from N,N-dimethylformamide-water gave the monohydrate of the title compound as a pale yellow powder; mp>380° C. Analysis for ($C_{16}H_{14}N_4O_4H_2O$):C, 55.81; H, 4.68; N, 16.27. Found: C, 56.05: H, 4.69; N, 16.27. The structure was confirmed by $^1$H-NMR and EI mass spectrum.

Alternatively, the 1,3-dimethylxanthyl cinnamic acid can be prepared by refluxing 5,6-diamino-1,3-dimethyluracil hydrate (5.11 g, 30.0 mmol) and 4-formylcinnamic acid (5.29 g, 30.0 mmol) in nitrobenzene (500 mL). The nitrobenzene was allowed to distill slowly with water formed. Fresh nitrobenzene was added to keep the volume constant. After 5 hours of reflux, the mixture was cooled and the precipitate collected (8.07 g). Recrystallization from N,N-dimethylformamide-water gave the monohydrate as a pale yellow powder, identical with that prepared by the method described above by $^1$H-NMR and elemental analysis.

EXAMPLE 2

Preparation of
(E)-4-(1,2,3,6-tetrahydro-2,6-dioxo-1,3-dipropyl-9H-purin-8-yl) cinnamic acid (4-DPPC)

(E)-4-(1,2,3,6-tetrahydro-2,6-dioxo-1,3-dipropyl-9H-purine-8-yl)cinnamic acid was prepared by following an analogous procedure to that for preparing the 1,3-dimethylxanthyl cinnamic acid. The 1,3-dipropyl compound was prepared with a melting point of 355° C. (dec.).

Analysis for ($C_{20}H_{22}N_4O_4$) C, 62.82; H, 5.80; N, 14.65. Found: C, 62.91; H, 5.84; N, 14.63.

Testing Procedure I:

Mongrel dogs weighing 20 to 26 Kg were anesthetized with intravenous sodium pentobarbital (25–30 mg/Kg), intubated, and mechanically ventilated at a rate sufficient to maintain $PaCO_2$ at 35 to 45 mmHg and pH between 7.35 and 7.45. The right femoral artery was cannulated for determination of arterial blood pressure. ECG lead II was continuously monitored. VF was induced by low voltage alternating current through a 6 Fr bipolar electrode catheter introduced into the right carotid artery and advanced into the left ventricle. The cessation of ventilation and clamping of the endotracheal tube preceded each induction of VF. Defibrillatory shocks of damped sinusoidal waveforms were administered with a Physio Control Lifepak 6 defibrillator via an apparatus which maintained balance and constant pressure of thoracic electrodes (50 newtons). A 6 Fr angiographic catheter was introduced into the right external jugular vein and advanced to the right atrium for purposes of drug administration. Rapid bolus infusions of 8-PST (5 mg/$Kg^{-1}$) were administered intravenously.

Protocols

Figure 1B:
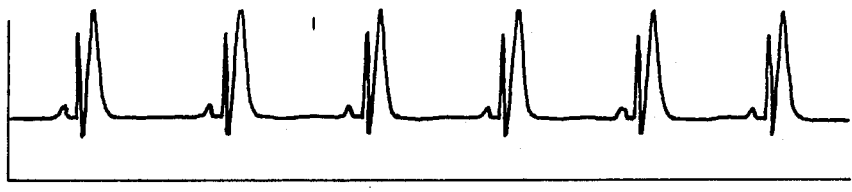

Prior to the experiments designed to elucidate the efficacy of adenosine antagonism, the threshold current for defibrillation was determined by delivering sequential incremental DC shocks for VF lasting less than 45 seconds. No depression of automaticity, conduction, or hemodynamic state was noted (FIG. 1). The current was measured in a storage oscilloscope for the waveform generated across a current sensitive resistor in series with a voltage divider network with known applied voltage. During subsequent experimentation, all shocks were administered with a peak current of 35 Amps (A) on the first two shocks and at 40 to 50 A on all subsequent shocks.

Experiments were divided into two groups of dogs; that is, Group A control dogs (no pre-treatment) and Group B dogs were pre-treated with 8-PST. In both groups, closed chest massage was not performed and DC shocks were initiated following 2 minutes of VF. In Group A, following defibrillation 8-PST was infused after marked bradycardia and hemodynamic collapse had developed. In a subset of dogs, ventilation was performed prior to 8-PST infusion. In Group B, the dogs were pre-treated with 8-PST (5 mg/Kg IV) 2 to 5 minutes before the induction of VF. Following defibrillation, if hemodynamic collapse persisted, ventilation without closed chest massage and/or a subsequent infusion of 8-PST was administered. Ventilation was routinely initiated following hemodynamic recovery.

Statistical analysis of variables was based on the Student's t-distribution for paired and unpaired data (15). Significant difference was considered for $p<0.05$. All values were expressed as the mean ±standard error of the mean (SEM).

Results

Dogs pre-treated with 8-PST (Group B) required significantly fewer countershocks (1.3±0.2; n =8) versus Group A (2.5±0.6; n =9), p <0.05) even though the pretest ventricular defibrillation threshold (VDT) for VF less than 45 seconds for Group A (23.2±1.2 A) and Group B (25.5±2.1 A) were similar. No dog in Group B required more than two shocks of 35 A to defibrillate. The duration of VF was significantly different for the two groups (157±25 secs for Group A and 125±3 secs for Group B; p <0.05).

In Group B, the post-defibrillation ventricular cycle length (583±47 msec; n =8) was only slightly different from the pre-8-PST (395±29 msec; n =8) and pre-VF (397±29 msec; n =8) cycle lengths. While transient AV block was seen immediately post-defibrillation, 6 of 8 animals from Group B exhibited sinus rhythm within 10 seconds following defibrillation. In contrast, severe bradycardia was noted post-defibrillation in Group A animals with 5 of 9 animals exhibiting high grade AV block, idioventricular and idionodal rhythms. The mean post-defibrillation ventricular cycle length for Group A was 2428±516 msec, n =9. Subsequent infusions of 8-PST, however, restored sinus rhythm in 4 of these 5 animals and reversed bradycardia in 7 of 9 animals shortening the post-defibrillation cycle length to 940±63 msecs. (FIG. 1.)

Figure 2:
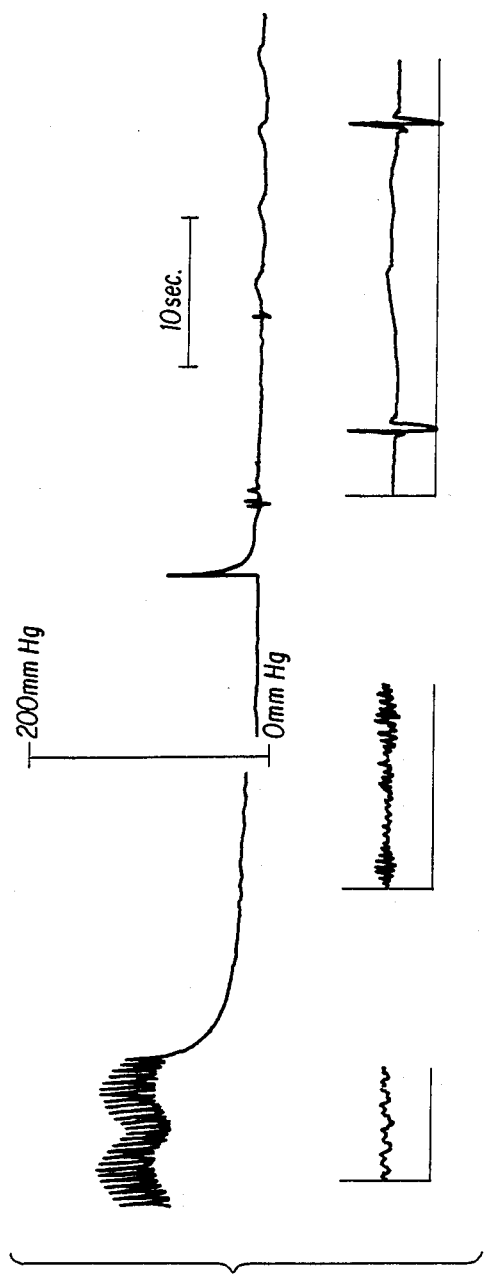
FIG. 2 illustrates the lack of effect of ventilation alone following canine cardiac defibrillation. Following defibrillation (3rd shock at 44 A), idioventricular rhythm (cycle length =4360 msecs; blood pressure =28/26 mmHg) appears. Ventilation alone had no effect on heart rate or blood pressure.

No animal from Group A exhibited hemodynamic recovery. The post-defibrillation pre-intervention blood pressure in Group A equalled 22±3/17 ±2 mmHg, n =9. Immediately after defibrillation, ventilation had no effect on blood pressure and failed to promote hemodynamic recovery. (FIG. 2.)

Figure 3:
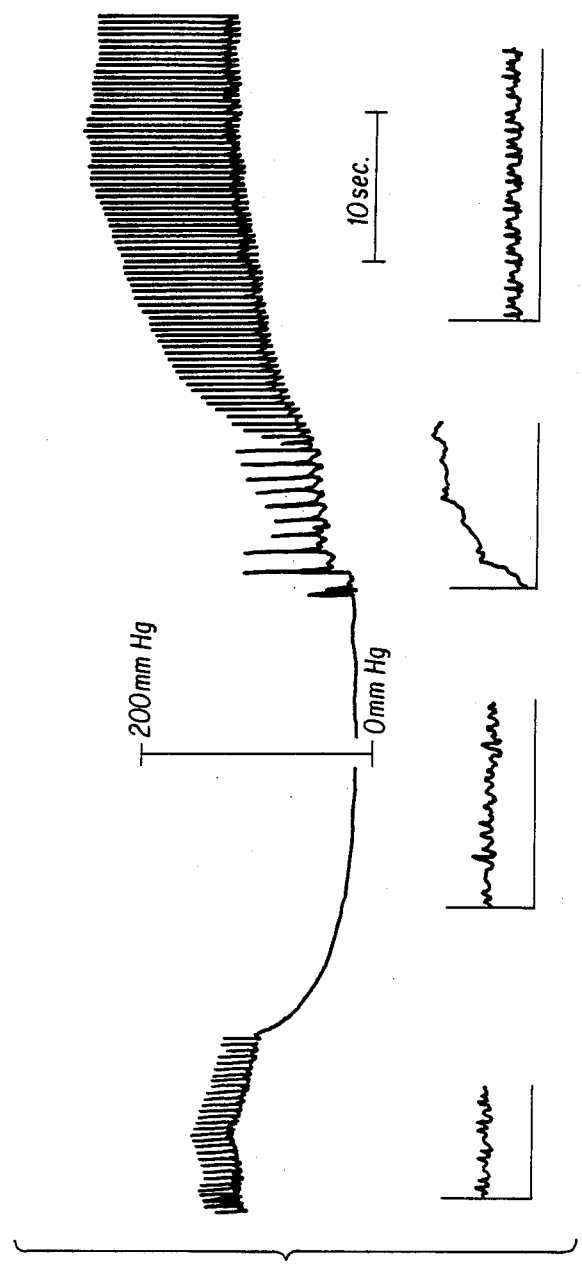
FIG. 3 illustrates the effect of 8-PST (5 mg/Kg) pre-treatment on canine post-defibrillation blood pressure. After defibrillation (35A) at 2 minutes, 2:1 AV block appears transiently, followed by sinus rhythm and a marked overshoot in blood pressure. Ventillation has not been re-initiated.
Figure 4A:
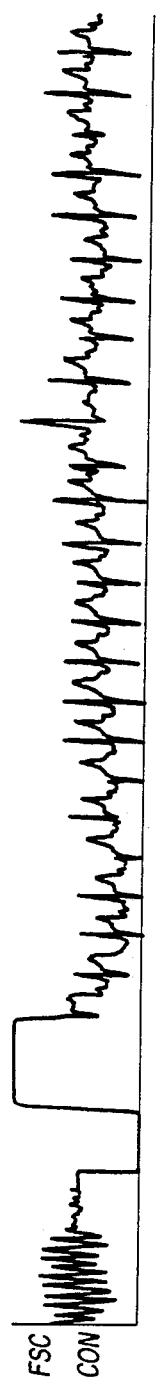
FIG. 4 illustrates 4-DPPC induced attenuation of porcine electrophysiologic depression following First (FSC) and Second Shock Conversions (SSC). Panel A: FSC — control. The sinus cycle length (SCL) at the 10th beat equals 500 msecs., and the PR interval equals 160 msecs. Panel B: FSC - Post 4-DPPC. At the 10th beat, the SCL and PR intervals are 360 and 120 msecs, respectively. Panel C: SSC control. Transient complete atrioventricular (AV) block is followed by 2:1 AV block at 15 secs post-defibrillation. Panel D: SSC - Post 4-DPPC. AV block is prevented. At the 10th beat, the SCL and PR intervals are 400 and 120 msecs, respectively.
Figure 4B:
Figure 4C:
Figure 4D:
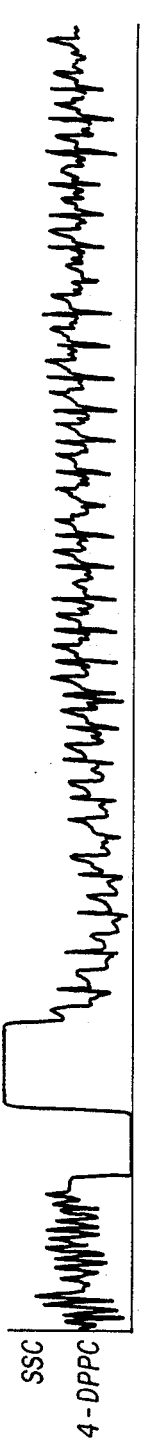

Most notably, pre-treatment with 8-PST (Group B) significantly improved the post-defibrillation hemodynamic state with 6 of 8 animals exhibiting complete recovery. Two of six required no interventions. (FIG. 3.) Two others recovered following the onset of ventilation while two required in addition a second bolus infusion of 8-PST. Prior to VF, 8-PST infusion had had no significant effect on blood pressure or heart rate.

The 6 animals with complete hemodynamic recovery displayed a marked overshoot in blood pressure (227±14/108±12 mmHg) which later reduced to 141±5/97±5 mmHg, approximating the pre-VF values (156±11/101±3 mmHg). In the 4 animals requiring ventilation and/or a second infusion of 8-PST, the post-defibrillation pre-intervention blood pressure equalled 53±6/26±4 mmHg. In the two animals which failed to recover despite intervention, the post-defibrillation, pre-intervention blood pressure averaged 28/24 mmHg. Of interest, no animal from Group B refibrillated after prior conversion of VF.

Only two animals in Group B required more than one countershock (i.e., 2 shocks) to defibrillate in 3 episodes of VF. The mean duration of VF in these animals was 137±4 secs., and the mean post-defibrillation, pre-intervention blood pressure was 105±57/51±20. Both recovered. Of the 3 animals from Group A which required 2 countershocks to defibrillate, the mean duration of VF was comparable (146±4 secs), but the mean post-defibrillation, pre-intervention blood pressure measured significantly less (23±2/19±3 mmHg; $p < 0.05$).

Two of nine animals from Group A, and 6 of 8 animals from Group B required one shock to defibrillate and thus had comparable VF durations (120 secs). The mean post-defibrillation, pre-intervention blood pressures for Groups A and B were significantly different (36±3/25±0 mmHg versus 81.0±35/ 43±18 mmHg respectively, $p < 0.05$).

Two of nine animals from Group A, and 6 of 8 animals from Group B required one shock to defibrillate and thus had comparable VF durations (120 secs). The mean post-defibrillation, pre-intervention blood pressures for Groups A and B were significantly different (36±3/25±0 mmHg versus 81.0±35/ 43±18 mmHg respectively, $p < 0.05$).

Testing Procedure II:

Domestic pigs of either sex weighing 45 to 55 pounds were intubated following mask induction with 3% halothane and supplemental intravenous surital and subsequently maintained on an inhaled anesthetic regimen of 0.3 to 0.6% halothane and a 1:1 mixture of oxygen and nitrous oxide. This anesthetic regimen has previously been used in the testing of defibrillation threshold in a porcine model (1). The lowest dose of halothane that maintained the mean aortic pressure greater than 90 mmHg in the absence of corneal reflexes was used. Ventilation via a Harvard respirator (model 944, Harvard Apparatus, South Natick, MA) was adjusted to maintain arterial pH and $pCO_2$ between 7.35 to 7.45 and 35 to 45 mmHg respectively. Fluid-filled angiographic catheters were advanced in the right femoral artery and right internal jugular veins for measurement of descending aortic and right atrial pressures respectively. Electrocardiographic lead II and pressures (Statham P23Db transducer, Statham Instruments, Inc., Oxnard, CA) were continuously monitored on an electrostatic recorder (Model 7758A, Hewlett-Packard, McMinnville, OR). A thermodilution Swan-Ganz catheter was advanced through the right femoral vein into the inferior vena cava for drug infusion and continuous measurement of central core temperature. New self-adherent R2 pads (Model 410, R2 Corporation, Morton Grove, IL) were firmly attached over the shaven right and left lateral thoracic walls at the transverse level of the heart and secured with an Ace Bandage.

Ventricular fibrillation (VF) was induced by applying alternating current through a percutaneous quadripolar catheter (No. 6F, United States Catheter and Instrument Corp., Billerica, MA) positioned in the right ventricle. The endotracheal tube was automatically clamped at peak-inspiration via a solenoid-switch at the induction of VF. Damped-sinusoidal DC shocks wee delivered by a commercially-available defibrillator (Model 43100A, Hewlett-Packard, McMinnville, OR) calibrated to deliver 3,000 V at 400 J across a 50 0 $\Omega$ load which was modified for prospective delivery of current through a constant-load current divider circuit as described by Lerman et al. (2). A rhythm strip of 15 secs duration was automatically produced with each defibrillation attempt. Voltage delivered across the thorax was measured with a 1,000:1 voltage divider in parallel with the defibrillator output, and the delivered current was measured with a 0.10 $\Omega$ resistor in series with the defibrillator output. Voltage and current waveforms were displayed on a triggered-sweep storage oscilloscope (Model 5113, Tektronix, Beaverton, OR) with a frequency response from DC to 1 MHz. Prior to defibrillation trials, transthoracic impedance was calculated from delivered energy and current following a synchronized DC shock at approximately 20 A during sinus rhythm. During the performance of each protocol, the variable resistors were then adjusted to deliver the desired current to the animal and simultaneously maintain a constant 50 0 load to the defibrillator. Thus, a slightly overdamped pulse was delivered (that was within 2% of the selected current) during each defibrillation trial, regardless of the transthoracic impedance.

Statistical Analysis. Statistical analysis of variables was based on student's t-distribution for paired and unpaired data (3). Significant difference was considered for p-values less than 0.05. All values were expressed as the mean ±standard error of the mean (SEM).

PROTOCOL NO. 1:

The objective of this protocol was to determine the effect of 4-DPPC on post-defibrillation rhythm disturbances associated with multiple repetitive ventricular fibrillation (VF) episodes. Temperature ranged from 33.5° to 35.5° C. for the protective effect of mild hypothermia on ventricular function. Temperature varied by no more than 1° C. in a given animal. Following the initial determination of transthoracic impedance, each animal was subjected to VF of 15 secs duration followed by a DC shock at 36A. Thereafter, following sequential 7.5 min recovery periods, VF episodes of 15 secs duration were followed by defibrillatory attempts at 2 A decrements until an initial shock failed. Upon the failure of any initial shock, ventilation and manual sternal compression at 80/min were initiated, followed by a rescue shock at 40 A, which was delivered at 26 to 30 secs of total VF duration. Subsequent testing was characterized by a 1 A increment following a precedent failure, and by a 1 A decrement following a precedent success. Basal threshold requirements (i.e., current-based defibrillation thresholds (DFT)) were determined by averaging the current values of at least 3 successful initial shocks which were followed by episodes demonstrating initial shock failures. After the basal DFT had been determined, either placebo or 4-DPPC (5 mg.kg$^{-1}$ dissolved in an alkalinized saline solution of pH 11.0 at a concentration of 2 mg/cc) was administered intravenously, and testing was continued with post-intervention threshold requirements determined as above.

PROTOCOL NO. 2:

The objectives of this protocol were to determine whether 4-DPPC could reverse post-defibrillation bradycardia and hemodynamic depression noted in the presence of dipyridamole, an adenosine-uptake blocker. Temperature ranged from 36° to 37° C. in all animals. In order to counter the undesirable hypotensive actions of dipyridamole (Boerhinger Ingelheim) and methoxamine (Burroughs-Wellcome Co.) at 0.015 mg.kg$^{-1}$.min$^{-1}$ IV were infused intravenously. After 10 minutes of methoxamine infusion, intravenous dipyridamole was administered as sequential 0.5 mg boluses at 30 to 60-second intervals until blood pressure returned to premethoxamine levels. VR of 45 secs duration was initiated followed by a DC shock at 40 A. Post-shock sequelae (rhythm disturbances and hemodynamic depression) were observed without intervention for 30 seconds. If systolic pressure equalled or exceeded 40 mmHg, a rapid intravenous bolus of 4-DPPC (5 mg.kg.$^{-1}$) was injected and the response noted. If systolic pressure was less than 40 mmHg, 4-DPPC was infused followed by no more then 30 secs of chest compression, which was performed to promote drug delivery. After recovery (7.5 minutes), additional intravenous dipyridamole (2 to 3 mg) was administered in divided doses to demonstrate continued antagonism of dipyridamole's hypotensive effect. A second VF episode of 45 secs duration was then repeated, followed by DC shock at 40 A.

RESULTS OF PROTOCOL NO. 1:

4-DPPC failed to significantly reduce DFT when compared to placebo (Table 1). Thus, an effect of adenosine antagonsim on defibrillation threshold may not be present with short ventricular fibrillation durations as endogenous adenosine release may be insufficient to alter current requirements. In contrast, 4-DPPC substantially reversed post-defibrillation depression of sinus node (SN) automaticity and atrioventricular (AV) nodal conduction (FIG. 4; Table 2). For example, with regard to first shock conversions (FSC), 4-DPPC significantly reduced the PR interval (102.5 ± 2.5 msec vs 143.8±9.0 msec, N=5, p =0.012) and sinus cycle length (360.0±8.2 msec vs 447.5±9.5 msec, N=5, p =0.003) compared to control when intervals at the 10th beat following successful defibrillation were analyzed.

Figure 5A:
FIG. 5 illustrates the complete atrioventricular (AV) block in a porcine heart the absence of an escape rhythm following a Second Shock Conversion (SSC): Reversal by 4-DPPC. Panel A: SSC - control. Note that there is no ventricular depolarization within the first 15 secs. post-defibrillation. At the 10th p-wave, the SCL equals 520 msecs. Panel B: SSC - post 4-DPPC. Only transient AV block is noted within the first 2 secs. At the 10th beat, the SCL and PR intervals are 400 and 120 msecs , respectively.
Figure 5B:

The effect of 4-DPPC on reversing A-V nodal conduction disturbances was more pronounced when a second DC shock was required, i.e. for second shock conversions (SSC) (FIG. 4,5; Table 2). In 47% (9 of 19) of control SSC episodes, less than 10 beats were noted in the first 15 secs. Of these 9 episodes, 7 exhibited high-grade (>2:1) AV block and the remaining two displayed complete AV block without ventricular capture during the first 15 secs post-defibrillation (FIG. 5). By contrast, in the presence of 4-DPPC no SCC episode exhibited less than 10 beats during the first 15 secs after defibrillation, and in only one of 16 episodes was a rhythm other than sinus (i.e. 2:1 AV block) noted at the 10th beat. 4-DPPC significantly increased the number of beats observed in the first 15 secs after defibrillation and significantly reduced PR interval and SCL in the 15 of 16 episodes in which sinus rhythm was present at a 10th beat (Table 1). In addition, the mean cycle length of the first 3 beats post-defibrillation was significantly shorter after 4-DPPC (Table 1).

Figure 7A:
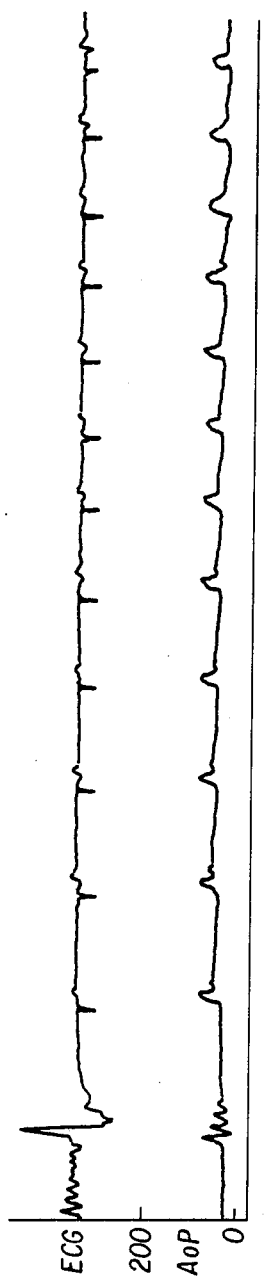
FIG. 7 illustrates the reversal of porcine Post-defibrillation electrophysiologic and hemodynamic depression by 4-DPPC in the presence of dipyridamole. Panels A and C display post-shock sequelae following 45 secs. of ventricular fibrillation (VF) after the intravenous infusion of dipyridamole (1.5 mg) during concomitant infusion of methoxamine, 0.015 mg kg$^{-1}$ min$^{-1}$. 40A shocks were delivered at the arrows. Panel A: Effect of dipyridamole. Initial 3:1 atrioventricular (AV) block is followed by 2:1 AV block and an aortic pressure (AoP) of 70/30 mmHg at 15 secs post-fibrillation. Panel B: Reversal of depression following 4-DPPC injection. 4-DPPC (5 mg kg$^{-1}$ IV) is injected prior to the beginning of the panel (30 secs post-defibrillation. The AoP had fallen to 60/25 mmHg. Post-injection in the absence of chest compression, the AoP rises to 125/95 mmHg, and the sinus cycle length (SCL) equals 410 msecs at the end of the cycle. Panel C: Prevention of depression after 4-DPPC pretreatment. Fifteen seconds after defibrillation transient 3:1 AV block has been supplanted by sinus rhythm (SCL, 400 msecs) and an AoP of 125/90 mmHg.
Figure 7B:
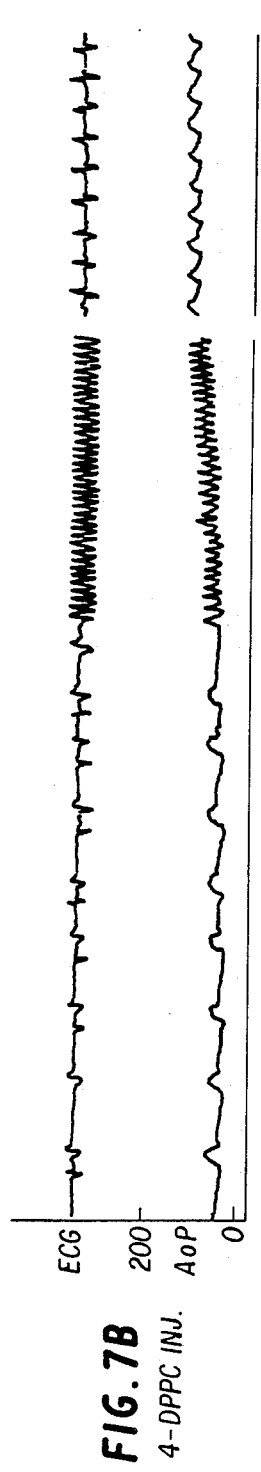
Figure 7C:
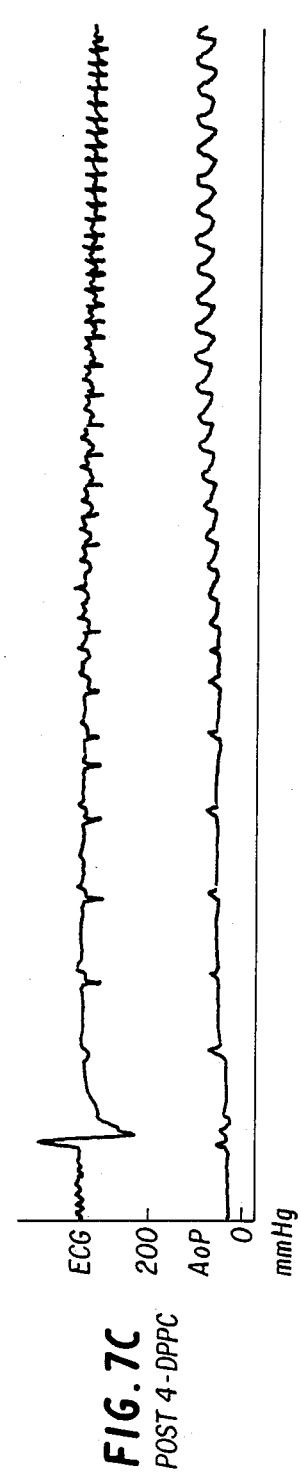

PROTOCOL NO. 2:

Methoxamine infusion significantly increased sinus cycle length (SCL) and aortic pressures prior to the administration of dipyridamole (Table 2). In response to dipyrimadole (1.5 to 7.5 mg), blood pressure returned to pre-methoxamine levels; however, SCL significantly lengthened further. During the first defibrillation period following dipyridamole administration (post VF1), the average heart rate and blood pressure during the first 15 secs after defibrillation were 30% and 50% less compared to 4-DPPC pretreatment values (post VF2) respectively (Table 2). In response to rapid infusions of 4-DPPC during the first post-defibrillation period (post VF1), both heart rate and aortic pressure rose markedly within 30 seconds post-injection (FIGS. 6, 7; Table 3). In 3 of 5 experiments, reversal of post-defibrillation hemodynamic collapse after 4-DPPC injection occured during concomitant manual chest compression that was performed to facilitate drug delivery because of inadequate pulse pressure (i.e. systolic pressure <40 mmHg). However, in two other instances, when pulse pressure was adequate for drup delivery (i.e. systolic pressure >40 mmHg), 4-DPPC also reversed hemodynamic collapse. In one instance, this occurred following a further deterioration in blood pressure (FIG. 7), and in another after prior injection of an equivalent volume of 4-DPPC diluent (placebo) had demonstrated no effect. Overall in 2 cases tested, an equivalent volume of placebo (i.e., 4-DPPC diluent) had no effect on post-defibrillation heart rate or blood pressure. Prior to the second episode of VF (VF2), in the presence of 4-DPPC pretreatment during sinus rhythm, intravenous dipyridamole (2 to 3 mg) had no effect on heart rate or blood pressure (Table 2).

TABLE 1

Absence of an Effect of 4-DPPC on Current-Based Defibrillation Threshold

| Control | vs. | 4-DPPC |
|---|---|---|
| 28.1 ± 1.1A | | 26.4 ± 0.6 A (NS, N = 5) |
| Control | vs. | Placebo |
| 30.9 ± 1.4 | | 29.2 ± 1.9 A (NS, N = 5) |

NS = No significant difference. All values expressed as mean ± standard error of the mean.

TABLE 2

4-DPPC-Induced Attenuation of Post-defibrillation Electrophysiologic Depression
PROTOCOL NO. 1

| | FSC Pre ANT | FSC Post ANT | SSC Pre ANT | SSC Post ANT |
|---|---|---|---|---|
| PR (msec) | 143.8 ± 9.0 | 102.5* ± 2.5 | 167.4 ± 11.6 | 103.0* ± 2.3 |
| SCL (msec) | 447.5 ± 9.5 | 360.0* ± 8.2 | 487.4 ± 22.8 | 385.4* ± 10.0 |
| Mean CL 1-3 (msec) | | | 2637.8 ± 385.5 | 930.2* ± 222.9 |
| No. of beats (15 secs) | | | 14.2 ± 3.2 | 33.2* ± 1.9 |

Abbreviations:
FSC, first shock conversions;
SSC, second shock conversions;
ANT, antagonist (i.e. 4-DPPC);
Pr, P-R interval noted at the 10th beat post-defibrillation;
SCL, sinus cycle length noted at the 10th beat post-defibrillation;
mean CL 1-3, mean cycle length of the first 3 beats post-defibrillation.
*p < 0.02 vs. Pre ANT, N = 5.

TABLE 3

4-DPPC-Induced Reversal of Post-Defibrillation Electrophysiologic and Hemodynamic Depression in the Presence of Dipyridamole
PROTOCOL NO. 2

| | Pre MET | Post MET | Pre VF1 Post DPM | VF1 | Post Shock- Pre ANT | Post Shock- Post ANT | Pre VF2 ANT | Pre VF2 ANT + DPM | VF2 |
|---|---|---|---|---|---|---|---|---|---|
| CL (msec) | 404.0 ± 13.3 | 472.0 ± 39.3 | 608.0 ± 40.8 | | | | 568.0 ± 52.7 | 571.2 ± 49.8 | |
| AoP syst. (mmHg) | 116.0 ± 6.6 | 135.0 ± 8.9 | 117.00** ± 13.1 | | | | 129.0 ± 12.0 | 137.5 ± 16.5 | |
| AoP diast. (mmHg) | 85.2 ± 8.0 | 103.0 ± 7.0 | 78.0** ± 13.1 | | | | 96.3 ± 10.6 | 100.0 ± 13.7 | |
| AoP mean (mmHg) | 98.0 ± 7.8 | 117.4 ± 7.6 | 97.0** ± 11.7 | | | | 112.0 ± 10.3 | 117.5 ± 14.6 | |
| RAP mean (mmHg) | 7.6 ± 0.8 | 8.2** ± 0.9 | 10.2 ± 1.2 | | | | 11.4 ± 1.3 | 9.8 ± 1.2 | |
| Heart Rate (ppm) | | | | 43.2 ± 20.4 | 48.2° ± 15.1 | 111.2* ± 10.3 | | | 123.2* ± 8.4 |
| AoP syst. (mmHg) | | | | 58.0 ± 17.2 | 66.6° ± 17.5 | 113.0* ± 12.0 | | | 110.0* ± 6.7 |
| AoP diast. | | | | 9.4 | 11.5 | 16.9 | | | 8.2 |

Abbreviations:
MET, Methoxamine;
DPM, dipyridamole;
ANT, antagonist (4-DPPC);
VF1, post first ventricular fibrillation episode (45 secs duration);
VF2, post second VF episode (45 secs duration);
CL, cycle length;
AoP, aortic pressure;
syst., systolic;
diast., diastolic,
RAP, right atrial pressure;
bpm, beats per minute.
Values for VF1 and VF2 were obtained at 15 secs post-defibrillation.
Values for Post-Shock-Post-ANT were obtained 30 secs following the intravenous injection of the 4-DPPC.
*$p < 0.02$ vs. VF1;
°no significant difference ($p > 0.05$) vs. VF1;
$p < 0.03$ vs. Pre MET;
**no significant difference ($p > 0.05$) vs. Pre MET;
N = 5.

Obviously, numerous modifications and variations of the present invention are possible in light of the above teachings. It is therefore to be understood that within the scope of the appended claims, the invention may be practiced otherwise than as specifically described herein.

REFERENCES

1. Geddes, L. A., W. A. Tacker, J. Rosborough, P. Cabler, R. Chapman, and R. Rivera. 1976. The increased efficacy of high-energy defibrillation. Med. Biol. Eng. May 1076:330–333.
2. Lerman, B. B., H. Halperin, J. Tsitlik, K. Brin, C. Clark, and O. C. Deale. 1987. Relationship between canine transthoracic impedance and defibrillation threshold. J. Clin. Invest. 80:797–803.
3. Daniels, W. W. 1983. Biostatistics: A Foundation for Analysis in the Health Sciences. John Wiley & Sons, New York. 1-534.

What is claimed as new and desired to be secured by Letters patent of the United States is:

1. A method of enhancing the efficacy of cardiopulmonary resuscitation, comprising:
    administering to a human or animal with post-resuscitation asystole or cardiac arrhythmia an amount of an adenosine antagonist sufficient to alleviate said asystole and cardiac arrhythmia wherein said antagonist competitively inhibits adenosine or reduces the level of adenosine present in myocardial tissue and associated fluids.
2. The method of claim 1, wherein said antagonist is a xanthine derivative or non-xanthine derivative.
3. The method of claim 2, wherein said antagonist is a methylxanthine.
4. The method of claim 3, wherein said methylxanthine is selected from the group consisting of 1,3,7-trimethylxanthine; 3,7-dimethylxanthine; 1,3-dimethylxanthine; aminophylline; and 8-(p-sulfophenyl)-theophylline.
5. The method of claim 2, wherein said antagonist is a propylxanthine.
6. The method of claim 2, wherein said antagonist is (E)-4-(1,2,3,6-tetrahydro-1,3-dimethyl-2,6-dioxo-9H-purin-8-yl)cinnamic acid or (E)-4-(1,2,3,6-tetrahydro-2,6-dioxo-1,3-dipropyl-9H-purine-8-yl)cinnamic acid.
7. The method of claim 2, wherein said antagonist is a non-xanthine derivative.
8. The method of claim 7, wherein said non-xanthine derivative is selected from the group consisting of imidazopyrimidine, pyrazolopyridine, etazolate, pyrazoloquinoline and triazoloquinazoline.
9. The method of claim 1, wherein said antagonist is administered in a dose of about 0.1–20 mg/kg.
10. The method of claim 9, wherein said antagonist is administered in a dosage of from about 0.45–10 mg/kg.
11. The method of claim 9, wherein said antagonist is administered in a dosage of about 3–5 mg/kg.
12. The method of claim 1, wherein said administration is selected from the group consisting of intravenous injection, oral ingestion, local release and insertion of a suppository.
13. The method of claim 12, wherein said administration is by intravenous injection.
14. The method of claim 13, wherein said intravenous injection is a continuous intravenous injection.
15. The method of claim 14, wherein said continuous intravenous injection is at a rate of about 0.45 mg/kg/hr.

16. The method of claim 1, wherein said administering occurs concurrently with an α-adrenergic, β-adrenergic or dopaminergic agent.

17. The method of claim 16, wherein said adrenergic or dopaminergic agent is administered in a ratio of about 0.01:1.0 to 1.0:0.01 relative to said antagonist.

18. The method of claim 1, wherein said enhancing comprises enhancing the effectiveness of cardioversion, defibrillation, and cardiac pacing within the setting of resuscitation.

19. A method for the treatment of post-resuscitation asystole, bradyarrhythmias, electro-mechanical dissociation, and hemodynamic collapse, comprising:
administering to a human or animal with post-resuscitation asystole or cardiac arrhythmia an amount of an adenosine antagonist sufficient to alleviate said asystole and cardiac arrhythmia wherein said antagonist competitively inhibits adenosine or reduces the level of adenosine present in myocardial tissue and associated fluids.

20. The method of claim 19, wherein said antagonist is a xanthine derivative or a non-xanthine derivative.

21. The method of claim 20, wherein said antagonist is a methylxanthine.

22. The method of claim 21, wherein said methylxanthine is selected from the group consisting of 1,3,7-trimethylxanthine; 3,7-dimethylxanthine; 1,3-dimethylxanthine; aminophylline; and 8-(p-sulfophenyl)-theophylline.

23. The method of claim 19, wherein said antagonist is a propylxanthine.

24. The method of claim 23, wherein said propylxanthine is (E)-4-(1,2,3,6-tetrahydro-1,3-dimethyl-2,6-dioxo-9H-purin-8-yl)cinnamic acid or (E)-4-(1,2,3,6-tetrahydro-2,6-dioxo-1,3-dipropyl-9H-purine-8-yl)cinnamic acid.

25. The method of claim 20, wherein said antagonist is a non-xanthine derivative.

26. The method of claim 25, wherein said non-xanthine is selected from the group consisting of imidazopyrimidine, pyrazolopyridine, etazolate, pyrazoloquinoline and triazoloquinazoline.

27. The method of claim 19, wherein said antagonist is administered in a dose of about 0.1–20 mg/Kg.

28. The method of claim 27, wherein said antagonist is administered in a dose of from about 0.45–10 mg/Kg.

29. The method of claim 27, wherein said antagonist is administered in a dose of about 3–5 mg/Kg.

30. The method of claim 19, wherein said administration is selected from the group consisting of intravenous injection, oral ingestion, local release and insertion of a suppository.

31. The method of claim 30, wherein said administration is by intravenous injection.

32. The method of claim 31, wherein said intravenous injection is a continuous intravenous injection.

33. The method of claim 32, wherein said continuous intravenous injection is at a rate of about 0.45 mg/Kg/hr.

34. The method of claim 19, wherein said administering occurs concurrently with an α-adrenergic, β-adrenergic or dopaminergic agent.

35. The method of claim 34, wherein said adrenergic or dopaminergic agent is administered in a ratio of about 0.01:1.0 to about 1.0–0.01 relative to said antagonist.

* * * * *

UNITED STATES PATENT AND TRADEMARK OFFICE
CERTIFICATE OF CORRECTION

PATENT NO. : 4,980,379
DATED : December 25, 1990
INVENTOR(S) : Luiz Belardinelli et al.

It is certified that error appears in the above-identified patent and that said Letters Patent is hereby corrected as shown below:

Column 1,
Line 7, the following paragraph is inserted immediately after the title:
-- U.S. Government Rights
This invention was made with United States Government support under Grant No. HL01408 and HL31111, awarded by the National Institutes of Health. The United States Government has certain rights in the invention. --

Signed and Sealed this

Sixth Day of July, 2004

JON W. DUDAS
*Acting Director of the United States Patent and Trademark Office*